United States Patent
Martin et al.

(10) Patent No.: US 9,244,052 B2
(45) Date of Patent: Jan. 26, 2016

(54) GLOBAL CRUDE OIL QUALITY MONITORING USING DIRECT MEASUREMENT AND ADVANCED ANALYTIC TECHNIQUES FOR RAW MATERIAL VALUATION

(71) Applicant: ExxonMobil Research and Engineering Company, Annandale, NJ (US)

(72) Inventors: Gregory M. Martin, Centreville, VA (US); James M. Brown, Flemington, NJ (US); Arthur H. Rose, Clifton, VA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 498 days.

(21) Appl. No.: 13/716,348

(22) Filed: Dec. 17, 2012

(65) Prior Publication Data

US 2013/0179092 A1   Jul. 11, 2013

Related U.S. Application Data

(60) Provisional application No. 61/579,413, filed on Dec. 22, 2011.

(51) Int. Cl.
*G01N 31/00* (2006.01)
*G01N 33/28* (2006.01)
*G01N 21/3577* (2014.01)

(52) U.S. Cl.
CPC ........ *G01N 33/2823* (2013.01); *G01N 21/3577* (2013.01)

(58) Field of Classification Search
None
See application file for complete search history.

(56) References Cited

U.S. PATENT DOCUMENTS 4,701,838 A   10/1987   Swinkels et al.
4,800,279 A   1/1989   Hieftje et al.
(Continued)

FOREIGN PATENT DOCUMENTS

EP   0305090 B1   8/1993
EP   0304232 B1   12/1996
(Continued)

OTHER PUBLICATIONS

PCT Written Opinion issued May 22, 2013 in corresponding PCT Application No. PCT/US2012/070231.
(Continued)

*Primary Examiner* — Aditya Bhat
(74) *Attorney, Agent, or Firm* — Glenn T. Barrett; Andrew T. Ward

(57) ABSTRACT

A method for monitoring global crude oil quality. The method includes the steps of obtaining samples of a crude oil having a quality, generating characterization data from measurements of samples of the crude oil, determining values of properties of an assay of the crude oil using the data of step a), storing the values of the properties of the assay in a database, determining deviations of the values of the properties of the assay from the values of the properties of a recommended assay having a quality, determining a statistical significance of the deviations of the values of the properties of the assay from the values of the properties of the recommended assay to determine if the crude oil quality is different from the quality of the recommended assay, and determining if the statistical significance indicates a change in the economic valuation between the assay and the recommended assay.

11 Claims, 12 Drawing Sheets

(56) References Cited

U.S. PATENT DOCUMENTS

| | | |
|---|---|---|
| 4,963,745 A | 10/1990 | Maggard |
| 5,121,337 A | 6/1992 | Brown |
| 5,139,334 A | 8/1992 | Clarke |
| 5,223,714 A | 6/1993 | Maggard |
| 5,225,679 A | 7/1993 | Clarke et al. |
| 5,348,645 A | 9/1994 | Maggard et al. |
| 5,349,188 A | 9/1994 | Maggard |
| 5,360,972 A | 11/1994 | DiFoggio et al. |
| 5,452,232 A | 9/1995 | Espinosa et al. |
| 5,475,612 A | 12/1995 | Espinosa et al. |
| 5,490,085 A | 2/1996 | Lambert et al. |
| 5,596,196 A | 1/1997 | Cooper et al. |
| 5,641,962 A | 6/1997 | Perry et al. |
| 5,699,269 A * | 12/1997 | Ashe et al. .................. 702/30 |
| 5,699,270 A | 12/1997 | Ashe et al. |
| 5,892,228 A | 4/1999 | Cooper et al. |
| 6,070,128 A | 5/2000 | Descales et al. |
| 6,662,116 B2 | 12/2003 | Brown |
| 7,904,251 B2 * | 3/2011 | Martin et al. .................. 702/22 |
| 2006/0043004 A1 | 3/2006 | Rose et al. |
| 2006/0160137 A1 | 7/2006 | Martin et al. |

FOREIGN PATENT DOCUMENTS

| | | |
|---|---|---|
| WO | 9417391 A1 | 8/1994 |
| WO | 0039561 A1 | 7/2000 |
| WO | 0151588 A1 | 7/2001 |
| WO | 0170912 A1 | 9/2001 |

OTHER PUBLICATIONS

PCT International Search Report issued May 22, 2013 in corresponding PCT Application No. PCT/US2012/070231.

Buthman, "Making Data Normal Using Box-Cox Power Transformation", http://europe.isixsigma.com/library/content/c080416a.asp or NIST Engineering Statistics Handbook, http://www.itl.nist.gov/div898/handbook/eda/section3/boxcoxli.htm.

Koehler et al., "EWMA Control Charts for Autoregressive Process", Journal of the Operational Society, vol. 52, (2001), pp. 699-707.

* cited by examiner

GLOBAL CRUDE OIL QUALITY MONITORING USING DIRECT MEASUREMENT AND ADVANCED ANALYTIC TECHNIQUES FOR RAW MATERIAL VALUATION

CROSS-REFERENCE TO RELATED APPLICATIONS

This application is the non-provisional filing of, and claims the benefit of, Provisional Application No. 61/579,413 filed on Dec. 22, 2011.

FIELD OF THE INVENTION

The presently disclosed subject matter is directed to a method for monitoring and valuing crude oil quality based upon measured bulk properties and advanced analytical techniques. The method analyzes crude oil samples with available methodologies to characterize the chemical and physical properties of the crude oil. The presently disclosed subject matter further implements an automated process to utilize the test results from the samples to generate detailed crude oil characterization data.

BACKGROUND OF THE INVENTION

Within the petrochemical industry, there are many instances where a very detailed analyses of a process feed or product is needed for the purpose of making business decisions, planning, controlling and optimizing operations, and certifying products. Such a detailed analysis is referred to as an assay, a crude assay being one example thereof.

Traditionally, when a crude oil is assayed, it is distilled in two steps. A method such as ASTM D2892 (see Annual Book of ASTM Standards, Volumes 5.01-5.03, American Society for Testing and Materials, Philadelphia, Pa.) is used to isolate distillate cuts boiling below approximately 650° F. (343° C.). The residue from this distillation is further distilled using a method such as ASTM D5236 to produce distillate cuts covering the range from 650° F. to approximately 1000-1054° F. (343° C. to approximately 538-568° C.) and a vacuum residue cut. At a minimum, cuts corresponding to typical products or unit feeds are typically isolated, including LPG (Initial Boiling Point to 68° F.), LSR (68-155° F.), naphtha (155-350° F.), kerosene (350-500° F.), diesel (500-650° F.), vacuum gas oil (650° F. to 1000-1054° F.), and vacuum residue (1000-1054° F.+). Each distillate cut is then analyzed for elemental, molecular, physical and/or performance properties. The specific analyses conducted depend on the typical disposition of the cut. The data derived from these analyses will typically be stored in an electronic database where it can be mathematically manipulated to estimate crude qualities for any desired distillation range. For example, commercial crude assay libraries are available from Haverly Systems Inc., and HPI Consultants Inc., both of which provide tools for manipulating the data, as does Aspentech Inc. Assay data is published by Crude Quality Inc., by Shell Oil Company, and by Statoil. The property versus distillation temperature data is typically fit to smooth curves that can then be used to estimate the property for any desired distillation cut. Crude assays that are generated via the distillation of the crude oil are herein referred to as "wet" crude assays to distinguish them from assay generated by other means.

The intent of the crude assay is to generate data representative of current crude oil quality for use in making business decisions, planning, controlling and optimizing operations, and certifying products. This representative assay is herein referred to as a Recommended Assay. These Recommended Assays are utilized to determine appropriate product slates for a given crude oil and identify refineries that are suitable for processing such crude oils.

Crude oil is not a homogenous entity. Physical and chemical characteristics of a crude oil change during the production life of the field. These characteristics may also change based upon the location of the crude oil within the field. In addition, crude oils from different fields are often blended together to produce a particular grade of crude oil that is commercially offered for sale. Changes in production volumes, field maintenance, new wells being brought onstream, or changes in a given fields crude oil quality over time can have an additional and often dramatic impact on the quality of a given crude oil grade. When such changes occur, the Recommended Assay may no longer be representative of the current crude oil quality.

Historically, crude oil monitoring has usually limited to a handful of easily and quickly measured properties including API gravity, sediment and water, (BS&W), salt and sulfur. These properties are usually referred to as Inspection Properties. Frequently, the only measurements made are API gravity and water, which are required to properly determine the amount of oil being sold. While these two properties can provide some indication of changes in crude oil quality, these two properties are extremely limited and more detailed monitoring and tracking of crude oil is desirable to make informed crude oil purchase and refining business decisions. More detailed characterizations have typically involved a laboratory distillation based assay which is relatively expensive, and can take several weeks to months to complete. Performing an assay of this type on cargo purchases to monitor and value crude oil quality changes would be impractical due to the time delay in obtaining the data. Real time monitoring and valuation of crude oil is desirable to make informed crude purchase and refining business decisions.

A given crude oil grade may not exhibit changes in API gravity even when the yield structure may vary dramatically. API gravity changes are typically accompanied by a shift in yields, such that a lower API gravity typically indicates an increase of heavier boiling materials. However, situations can occur where yield structure changes do not exhibit associated changes in the gravity. An example would be where naphtha boiling range components (68-375° F.) may decrease, with an associated increase in diesel range material (375-530° F.), accompanied by a shift of resid material boiling in the 1050+° F. range decreasing with an increase in gas oil material (530-1050° F.). While the overall yield structure resulting from these yield changes would be significantly different, the API gravities may not exhibit large changes. Yield changes could have a material impact on crude oil value that in this case would not be evident from the API gravity measurement. As such, additional evaluation of other properties is needed to determine whether or not a particular crude oil is appropriate for the production of the desired product slate or the processing in a particular refinery.

Properties in addition to gravity are also used to evaluate whether a given crude oil is economically attractive or whether it can be processed in a given refinery. Sulfur, neutralization number, or metals are examples of properties that may vary with time and can impact the ability of a given refinery to process a crude oil. For example, not all refineries are capable of processing crude oils that have a high sulfur content. Similarly, not all refineries are capable of processing heavy crude oils. API gravity provides no indication of a change in these qualities, but changes in these values would affect the crude oil's economic value.

Presently, there are well over 1000 unique commercially available crude oil grades. This presents a logistical issue with monitoring crude oil quality, detecting significant deviations from expected quality, and properly evaluating these changes. It is desirable to have the ability to quickly and efficiently obtain a more detailed characterization of the crude oil and monitor the properties in an organized manner in order to provide more insight for crude oil valuation. There is a need for an automated system that generates the characterization data, detects quality deviations, and triggers notifications for follow-up actions to ensure that changes in crude oil properties are identified and reflected in business decisions is desirable such that suitable crude oils are used to produce desired product slates and processed in the desired refinery.

The current state of the art for monitoring crude oil quality varies from simple plots of time series data of easily measured inspection properties as gravity, to application of correlative techniques to laboratory measurements. These time series data are tracked on a large number of crude oils which have commercial interest and are available globally through an internal company intranet website. Many of the laboratory tests are very time consuming taking weeks or longer to generate useful results.

SUMMARY OF THE INVENTION

The presently disclosed subject matter is directed a method for monitoring and valuing changes in crude oil quality based upon measured bulk properties and advanced analytical techniques. This method benefits from the detailed crude oil characterizations obtained from the use of advanced techniques. These advanced analytical techniques include those based upon spectroscopy or a combination of spectroscopy and physical inspections. The presently discloses subject matter utilizes a work process that includes the following: analyzing current crude oil sample receipts with available analytical methodologies to generate characterization data indicative of the crude oil's chemical and physical properties; automatically processing the characterization data to estimate an assay indicative of current crude oil quality; automatically retrieving the globally generated characterization and estimated assay data and store it within a central database; calculating the economic differential between the current Recommended Assay and this recently generated assay estimate; plotting the time series values for all properties of interest by crude oil grade; analyzing the time series data and evaluating the current crude oil grade trends versus the current Recommended Assay values; and determining if a new Recommended Assay should be issued. A Recommended Assay is a single representation of yields and qualities used by all downstream business functions to characterize current typical crude oil quality. If a new Recommended Assay is needed, a wet assay may be performed, or the crude oil may be analyzed via the method disclosed in commonly assigned U.S. Pat. No. 6,662,116 to Brown, herein referred to as the "Virtual Assay" or by the method disclosed in commonly assigned U.S. Pat. No. 7,904,251 to Martin et al. herein referred to as "Modified Virtual Assay". Brown and Martin et al. are incorporated herein specifically by reference in their entireties.

The presently disclosed subject matter is directed to a method for monitoring global crude oil quality. The method includes obtaining at least one sample of a crude oil representative of the current quality of the crude oil. The method further includes analyzing the at least one sample of the crude oil and generating characterization data based upon the analyzing of the at least one sample. The values of properties of an assay of the crude oil are estimated by analyzing the generated characterization data from the at least one sample to form an estimated assay. These estimated values of the properties of the estimated assay are stored in a database. The method further includes determining deviations of the values of the properties of the estimated assay for the crude oil from the values of the properties of a known Recommended Assay for crude oil having a known quality. The values of the properties of the known Recommended Assay are also stored in the database. The statistical significance of the deviations of the values of the properties of the estimated assay from the values of the properties of the Recommended Assay is determined to determine if the crude oil quality of the at least one sample is different from the quality of the recommended assay. If the deviations of the values of the properties of the estimated assay from the values of the properties of the Recommended Assay are significant, then a new Recommended Assay for the crude oil is generated. The new Recommended Assay is stored in the database. The new Recommended Assay in the database may replace the known Recommended Assay as the new known Recommended Assay.

Determining the statistical significance of the deviations of the values of the properties of the estimated assay from the values of the properties of the Recommended Assay may include determining if the statistical significance indicates a change in the economic valuation of the crude oil between the estimated assay and the Recommended Assay. A notification may be generated if the economic difference is statistically significant. It is contemplated that values of properties that may distort the statistical significance of the economic difference may be identified and removed.

Determining deviations of the values of the properties of the estimated assay for the crude oil from the values of the properties of a known Recommended Assay for crude oil may include determining time series values for the properties of the estimated assay over a period of time. The properties of the time series values may be compared to values of the properties for the Recommended Assay.

The presently disclosed subject matter provides a systematic mechanism to leverage recent advances in analytic techniques that provide a detailed analysis of a crude oil, inexpensively, and in a timely fashion. Additionally, the presently disclosed subject matter implements automatic abnormal event detection and notification and includes a systematic approach to ensure consistency of results.

BRIEF DESCRIPTION OF THE DRAWINGS

FIGS. 6a and 6b show a statistical analysis of the Recommended Assay.

DESCRIPTION OF PREFERRED EMBODIMENT

Figure 1:
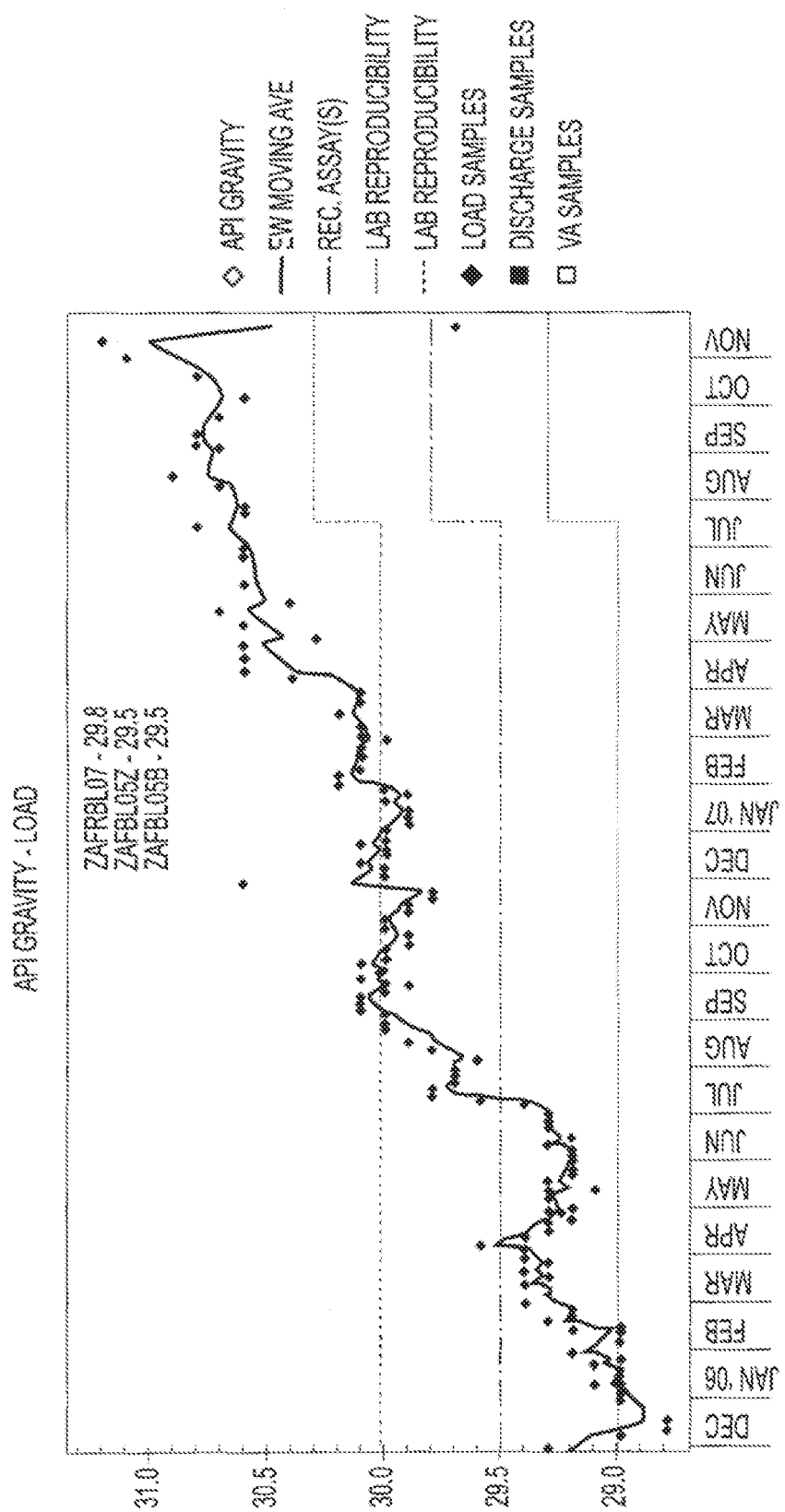
FIG. 1 shows a time series of crude oil monitoring data for API gravity of Zafiro crude oil blend.

Within the petrochemical industry, detailed feedstock quality analysis is required to make potential purchase decisions and to plan, control, and optimize refinery unit operations. Traditional "wet" crude assay analyses are costly and time consuming to perform, involving a laboratory distillation based which can take from several weeks to several months to complete. Alternate, more rapid and less expensive technologies have been developed to supplement the traditional approach.

Alternate methodologies to generate information similar to that of the detailed "wet" crude assay analysis in an inexpensive and timely fashion have been described by Brown and are referred to as Virtual Assay. These alternate methodologies are dependent upon the analysis of an unknown material using spectroscopy or a combination of spectroscopy and physical inspections. Furthermore, methods to modify a Virtual Assay have been described by Martin et al. and are referred to as a Modified Virtual Assay. The results of a Virtual Assay or Modified Virtual Assay can be used in a similar fashion to those of a wet crude oil assay, however, the detailed Virtual Assay or Modified Virtual Assay characterization results are available within hours rather than spanning several months. This represents a significant time savings.

A Recommended Assay is a single representation of yields and qualities used by all downstream business functions to characterize current typical crude oil quality. Recommended Assays can be either "wet" assays (laboratory distillation based), or Modified Virtual Assays. Assays are promoted to Recommended Assay status if they are representative of expected crude oil quality. When crude quality deviates significantly from the current Recommended Assay, a new Recommended Assay will be produced so as to provide optimal data for business decisions.

The presently disclosed subject matter describes a process to use these crude oil quality predictions and includes the following elements: generating detailed characterization data from measurements of load or discharge crude samples; developing a completed Virtual Assay or Modified Virtual Assay estimate of the crude oil assay; storing the assay information in a central database; applying statistical techniques to highlight significant deviations from the Recommended Assay for this crude oil grade; automatically notifying users of significant quality changes; applying a market value differential between the Recommended Assay and current assay estimate based on estimated quality changes and market pricing; updating the Recommended Assay as warranted; and employing laboratory checks to ensure consistency of results. Each of the steps of the process will be described in greater detail below. For purposes of this disclosure, crude oils and crude oil blends may be collectively referred to as "crude oil". It is contemplated that the presently disclosed subject matter is intended to be used in connection with Recommended Assays for both crude oils, crude oils and blends of crude oils with other materials where Recommended Assays are utilized for quality determination.

Generate Detailed Characterization Data from Sites Around the World

Many grades of crude oil, such as Arab Light, are internationally traded. Regional refinery labs are equipped with the necessary instrumentation to perform the spectroscopic and physical inspections required to generate a Virtual Assay. Upon completion of the spectroscopic and physical inspection measurements, the data and grade identification is automatically transferred to a suitable computer system for analysis to generate the Virtual Assay. Upon completion of the analysis, the assay results are stored in a laboratory information data repository. These results are used to determine whether or not any modifications are needed to the Recommended Assay, as described below.

Develop a Completed Crude Oil Assay

Current state of the art as reported in the literature includes, but is not limited to, analytical techniques involving NMR UV, visible and near mid infrared spectroscopy. In accordance with the presently disclosed subject matter, preferred methods are the Virtual Assay or the Modified Virtual Assay. In the following discussion, both the Virtual Assay and the Modified Virtual Assay shall be collectively referred to as "Virtual Assay."

While the processing required to generate a Virtual Assay from the laboratory measurements may be done locally at the refinery, the capability to capture this data and generate a Virtual Assay can also be done centrally. Simple continuous computing processes scan locations on a computer network for the necessary inputs, and generate the Virtual Assay when all required data are available. The inputs and estimated assay data are stored centrally in a computer system that is linked to each of the refineries and the sites where the samples are obtained. These inputs from multiple locations can be utilized to obtain a Virtual Assay on a received cargo within several hours of receipt. The resultant Virtual Assay is globally available.

The quality of the Virtual Assays generated through this method may vary. A mechanism is required to determine the quality of the Virtual Assay that is generated. This quality measure mechanism will enable proper evaluation of the results for making commercial decisions and is known as a Fit Quality Ratio, or FQR.

The spectral data in the 4685.2-3450.0 cm$^{-1}$, 2238.0-1549.5 cm$^{-1}$ and 1340.3-1045.2 cm$^{-1}$ regions were orthogonalized to corrections for baseline, liquid water and water vapor, concatenated to the weighted data for linearly blendable data for API gravity and viscosity, and fit as a linear combination of similarly orthogonalized and concatenated data for reference crudes using a Nonnegative Linear Least Squares algorithm.

$R^2$ is calculated as $$R^2 = 1 - \frac{\left(\begin{bmatrix}\hat{x}_u \\ w_{API}\hat{\lambda}_{u(API)} \\ w_{Visc}\hat{\lambda}_{u(Visc)}\end{bmatrix} - \begin{bmatrix}sx_u \\ w_{API}\lambda_{u(API)} \\ w_{Visc}\lambda_{u(Visc)}\end{bmatrix}\right)^T \left(\begin{bmatrix}\hat{x}_u \\ w_{API}\hat{\lambda}_{u(API)} \\ w_{Visc}\hat{\lambda}_{u(Visc)}\end{bmatrix} - \begin{bmatrix}sx_u \\ w_{API}\lambda_{u(API)} \\ w_{Visc}\lambda_{u(Visc)}\end{bmatrix}\right) \Big/ (f+2-c-1)}{\left(\begin{bmatrix}sx_u \\ w_{API}\lambda_{u(API)} \\ w_{Visc}\lambda_{u(Visc)}\end{bmatrix} - \begin{bmatrix}sx_u \\ w_{API}\lambda_{u(API)} \\ w_{Visc}\lambda_{u(Visc)}\end{bmatrix}\right)^T \left(\begin{bmatrix}sx_u \\ w_{API}\lambda_{u(API)} \\ w_{Visc}\lambda_{u(Visc)}\end{bmatrix} - \begin{bmatrix}sx_u \\ w_{API}\lambda_{u(API)} \\ w_{Visc}\lambda_{u(Visc)}\end{bmatrix}\right) \Big/ (f+2-1)} \quad [1]$$

$\lambda_u^{(api)}$ and $\lambda_u^{(visc)}$ are the volumetrically blendable forms of API gravity and viscosity, and $w_{API}$ and $w_{visc}$ are the weighting factors for the two inspections. $\hat{\lambda}_u^{(api)}$ and $\hat{\lambda}_u^{(visc)}$ are the estimated blendable forms of API gravity and viscosity calculated based on the Virtual Blend, where the Virtual Blend is a blend that exists only in theory, preferably on a computer.

A Fit Quality, FQ, is calculated as:

$$FQ = \sqrt{1 - R^2} \quad [2]$$

The Fit Quality Ratio, FQR, is calculated as:

$$FQR = \frac{FQ}{FQC} \quad [3]$$

FQC is a Fit Quality Cutoff. FQC is selected such that analyses with FQR≤1.0 will produce predictions of adequate precision for the intended application. Analyses for which FQR≤1.0 are referred to as Tier 1 analyses. For the library used in this example, FQC value of 0.0080 was selected such the precision of yield predictions for Tier 1 analyses is comparable to the reproducibility of the distillation. While the methodology of this invention preferably uses the results of Tier 1 analyses as input, Tier 2 analyses (FQR<1.5) are also used.

Store the Information in a Central Database

Once the Virtual Assay results have been generated, they are stored in a central database to enable retrieval and plotting. This database is designed to contain three types of data for each crude oil or crude oil blend: (1) detailed Virtual Assay characterizations; (2) measured inspection properties, crude grade, sampling date, sample location, loadport (e.g., the point of loading the crude oil on a vessel or pipeline) and disport (e.g., the point of off-loading the crude oil from the vessel or pipeline) information stored to enable categorization and data analysis; and (3) the Recommended Assay for the crude oil grade.

Figure 2:
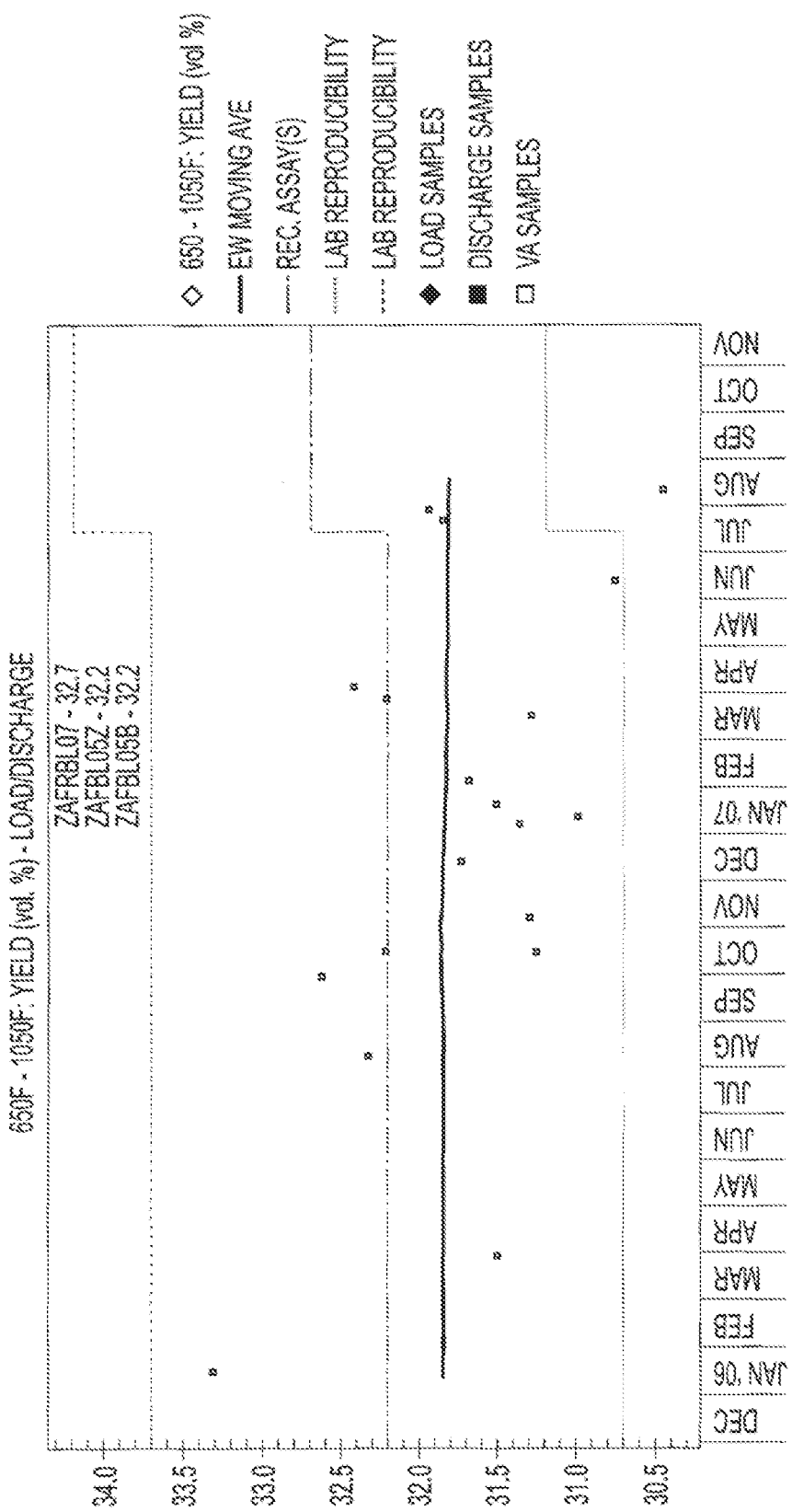
FIG. 2 shows a time series of crude oil monitoring data for VGO yield of Zafiro crude oil blend.
Figure 3:
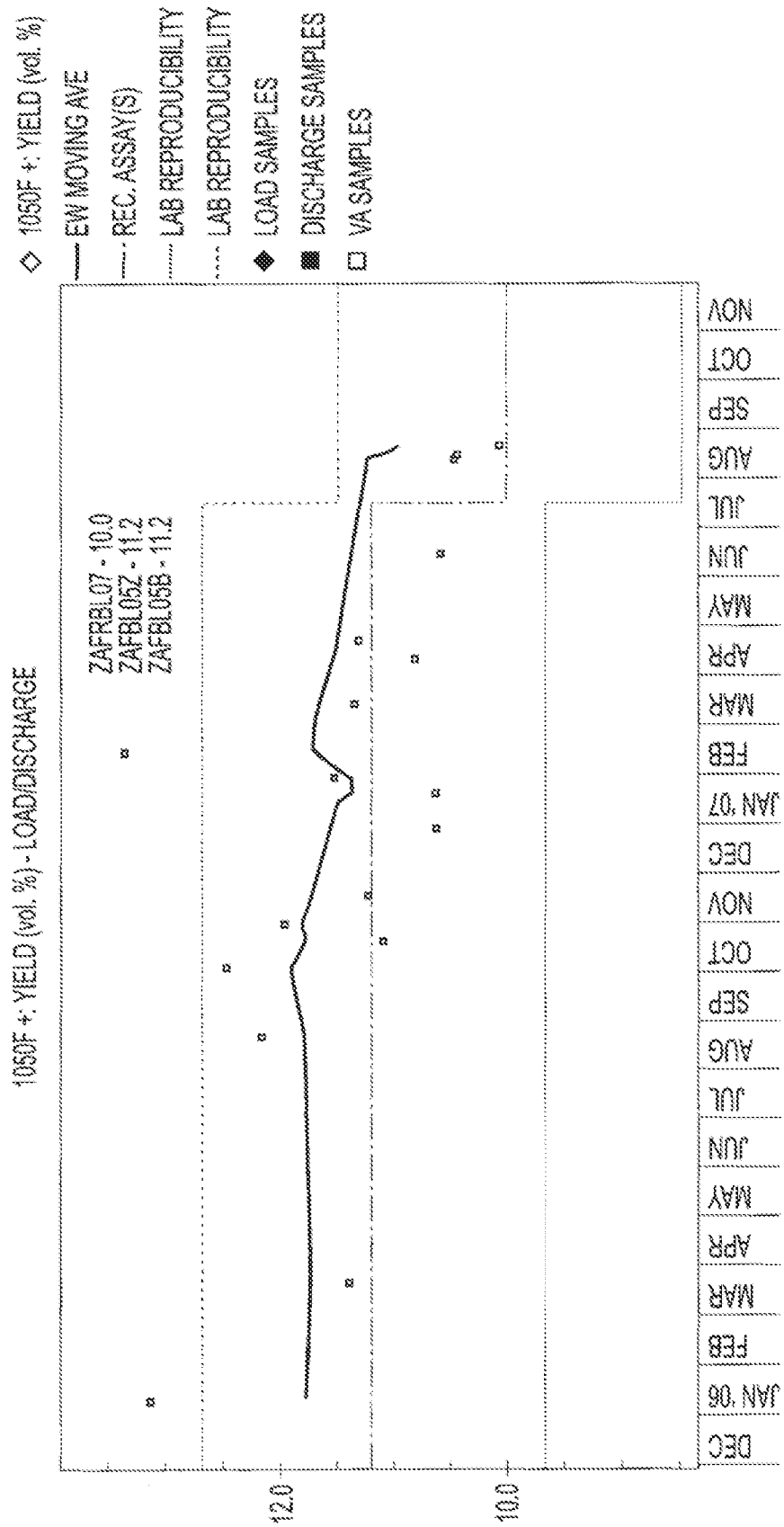
FIG. 3 shows a time series of crude oil monitoring data for resid yield of Zafiro crude oil blend.

Compare Time Series Values for Properties Selected by the User to Current Recommended Assay Data can be selected for display and would typically include grade, date range and property. The Recommended Assay is included as a baseline to show current crude oil quality differences versus the Recommended Assay over time. One display of data is presented in FIG. 1-3 for Zafiro Blend crude oil from Equitorial Guinea. These charts present the whole crude measured API gravity, gas oil yield (650 F to 1050 F) and resid yield (1050+F) over a two year time period. The data includes Virtual Assay data and physical inspection data, as well as the Recommended Assay values. Similar charts can be easily produced from the database for any property, time period or crude oil grade.

Apply Statistical Techniques to Highlight Significant Deviations from the Recommended Assay Variations in crude oil quality occur which may indicate a crude oil has changed versus the current Recommended Assay, or in the absence of a recommended assay, that a crude oil has a significant quality change compared to previous samples.

300 or more crudes are typically monitored on a routine basis, and over a hundred different qualities may be recorded. This would result in over 30,000 combinations of qualities and grades. It is infeasible to manually review each of thequalities for each grade to detect significant quality changes.

As such, statistical tests have been implemented to highlight significant deviations, and analyze the data to identify a quality change.

For each crude oil grade in the database, the following procedure may be executed for each property, each time a new datapoint is added.

Figure 4:
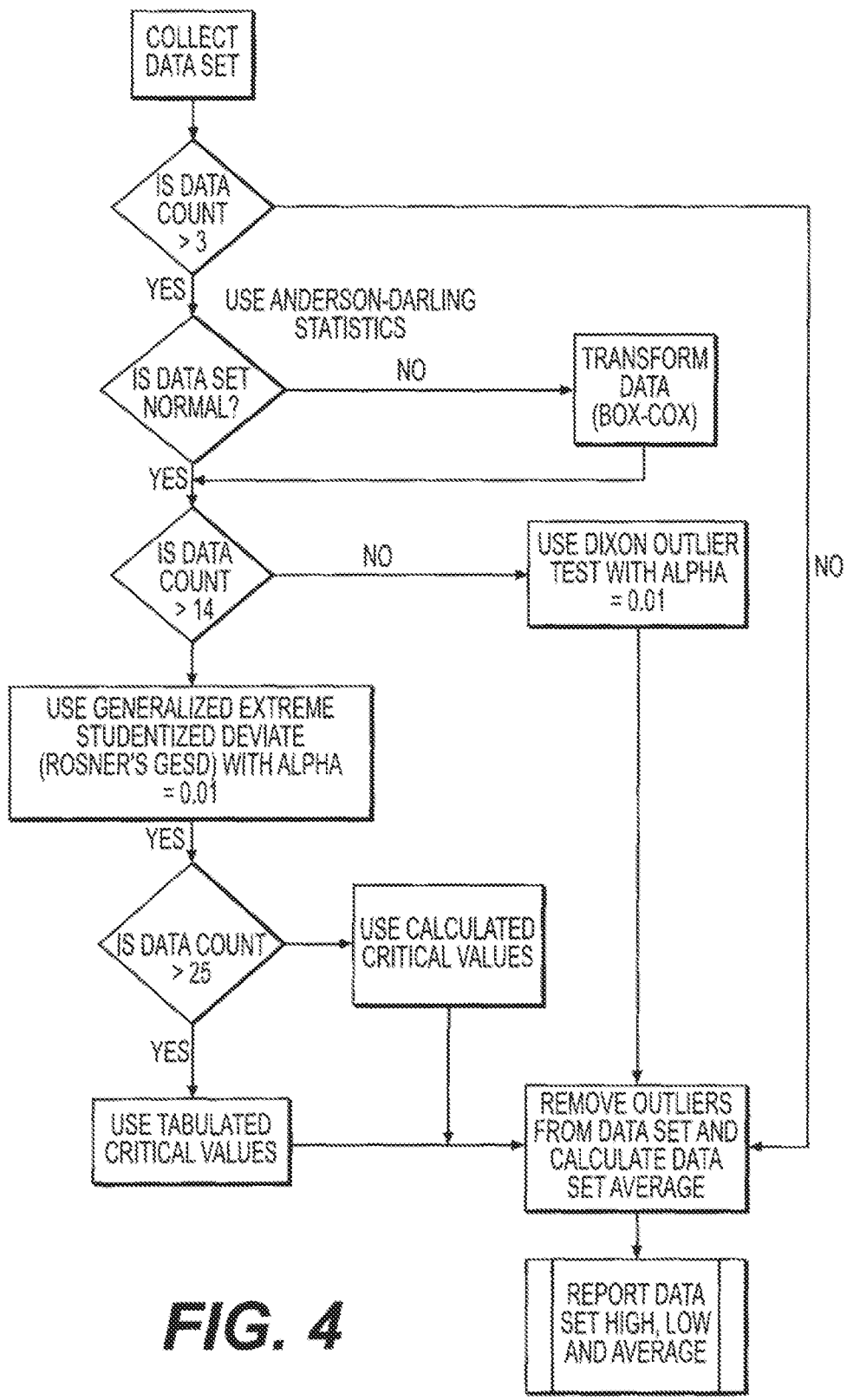
FIG. 4 shows a flowchart for data outlier algorithm in accordance with aspects of the presently disclosed subject matter.

In the following checklist, the "dataset" is defined as all data collected since the time that the current Recommended Assay was conducted. When a crude quality change has been identified and a new Recommended Assay has been declared, all previous data to that change is no longer significant to the analysis and is ignored in all calculations. FIG. 4 provides a flowchart for an algorithm to detecting and removing potential values which may be identified as outliers so they do not skew the data analysis.

1. Detect and remove outliers from the dataset. Check that the dataset is normally distributed. An Anderson-Darling test is suitable for this purpose. Anderson-Darling and other potentially suitable tests are described in "How to Test Normality and Other Distribution Assumptions" (S. Shapiro, The ASQC Basic Reference In Quality Control: Statistical Techniques). If the dataset is not normally distributed, then apply an appropriate transform to improve normality. A Box-Cox transform is suitable for this purpose (see for example, A. Buthmann, "Making Data Normal Using Box-Cox Power Transformation", http://europe.isixsigma.com/library/content/c080416a.asp or NIST Engineering Statistics Handbook, http://www.itl.nist.gov/div898/handbook/eda/section3/boxcox-li.htm). If the number of data points is greater than 3, but less than 14, apply the Dixon Outlier Test. If the number of data points exceeds 14, apply Rosner's Generalized Student Deviate Outlier Test. The outlier tests are described in "How to Detect and Handle Outliers" (B. Iglewicz and D. Hoaglin, Asqc Basic References in Quality Control, Vol 16).

2. Check and see if there is enough data to continue. For all properties where data is obtained from multiple data sources, a suitable minimum number of points is 10. For properties obtained from Virtual Assay only, a suitable minimum number of points is 5. These values are initial estimates for adequate representation of the data, therefore the flexibility for change to these values needs to be included.

3. After a new point, $p_n$, has been added for a given property, the average (mean) of the dataset, $\bar{p}$, is calculated as $$\bar{p} = \frac{\sum_{i=1}^{n} p_i}{n} \quad [4]$$

A check is done to see if the new dataset average is significantly different compared to the current Recommended Assay value. If R represents the reproducibility of the laboratory test method used to generate the property value, then a significant difference is defined as a mean value that differs from the Recommended Assay property value, $p_{RA}$, by more than $R(|\bar{p}-p_{RA}|>R)|$. When the same sample is tested independently by different laboratories, the results are expected to agree with R 19 times out of 20 (95% of the time). For standard methods published by consensus organizations such as ASTM, R will be the standard deviation of the dataset, $$\sigma = \sqrt{\frac{\sum_{i=1}^{n}(p_i - \bar{p})^2}{n-1}} \quad [4]$$

Calculate new control limits (UCL and LCL) for the new dataset. Control Limits are defined as the mean of the dataset +/−3 times the standard deviation of the dataset. Flag any points that are outside these control limits.

4. Calculate Moving Average, MA, as $$MA_1 = p_1$$

$$MA_1 = 0.4p_i + 0.6MA_{i-1}$$

Flag any MA points that differ from the dataset mean by more than R.

5. Flag any data points which constitute the 8th (or greater) occurrence of consecutive points on the same side of the dataset mean.

6. Flag any set of 10 data points that are consecutively increasing or decreasing.

7. If all of these checks are performed and no flags are set, then the dataset passes. Otherwise, the flag is logged into a report and distributed to the system administrator.

Example application of the checklist is shown in Table 1.

TABLE 1

Example of Checklist Application

Property X — 3) The Delta Between the Average and the RecAssay Value is > Tolerance (0.5 for this property). Could mean a quality change.

| Date | RecAssay | RecAssay Value | Sample Value | Sample Location | Average (Mean) of Dataset | UCL | LCL | Data Point Outside CL's? | Moving Average of Dataset | Outside 1/2 CL/Mean |
|---|---|---|---|---|---|---|---|---|---|---|
| 1/3/03 | ABCDEF03 | 20.0 | 20.4 | XXX | | | | | | |
| 1/8/03 | ABCDEF03 | 20.0 | 18.4 | ZZZ | | | | | | |
| 1/15/03 | ABCDEF03 | 20.0 | 20.5 | YYY | | | | | | |
| 2) 3 Outliers All From Same Sample Location. May want to eliminate those points from analysis. | | | 17.5 | ZZZ | | | | | | |
| | | | 19.9 | XXX | 20.6 | 26.9 | 14.2 | | 19.9 | |
| | | | 20.0 | XXX | 20.6 | 26.9 | 14.2 | | 19.9 | |
| | | | 19.5 | YYY | 20.6 | 26.9 | 14.2 | | 19.8 | |
| 3/21/03 | ABCDEF03 | 20.0 | 18.4 | ZZZ | 20.6 | 26.9 | 14.2 | | 19.2 | |
| 3/22/03 | ABCDEF03 | 20.0 | 19.6 | XXX | 20.6 | 26.9 | 14.2 | | 19.4 | |
| 4/16/03 | ABCDEF03 | 20.0 | 18.9 | XXX | 20.6 | 26.9 | 14.2 | | 19.2 | |
| 4/19/03 | ABCDEF03 | 20.0 | 20.4 | YYY | 20.6 | 26.9 | 14.2 | | 19.7 | |
| 4/21/03 | ABCDEF03 | 20.0 | 20.4 | XXX | 20.6 | 26.9 | 14.2 | | 20.0 | |
| 5/1/03 | ABCDEF03 | 20.0 | 20.3 | XXX | 20.6 | 26.9 | 14.2 | | 20.1 | |
| 5/6/03 | ABCDEF03 | 20.0 | 20.9 | YYY | 20.6 | 26.9 | 14.2 | | 20.4 | |
| 5/19/03 | ABCDEF03 | 20.0 | 20.6 | YYY | 20.6 | 26.9 | 14.2 | | 20.5 | |
| 6/2/03 | GHIJKL03 | 21.5 | 24.6 | XXX | 20.6 | 26.9 | 14.2 | | 22.1 | |
| 6/9/03 | GHIJKL03 | 21.5 | 24.8 | YYY | 20.6 | 26.9 | 14.2 | | 23.2 | |
| 6/15/03 | GHIJKL03 | 21.5 | 24.8 | XXX | 20.6 | 26.9 | 14.2 | | 23.8 | ALERT |

1) Need a minimum # of samples before analysis (5 in this case).

Analysis performed based on last data point in set.

5) A change in quality was identified. A New RA was assigned and the process starts over.

4) Moving Average crossed over halfway point between.

| Date | RecAssay | RecAssay Value | Sample Value | Sample Location | Average (Mean) of Dataset | UCL | LCL | Data Point Outisde CL's? | Moving Average of Dataset | MA Outside 1/2 CL/Mean |
|---|---|---|---|---|---|---|---|---|---|---|
| 6/2/03 | GHIJKL03 | 24.8 | 24.7 | XXX | | | | | | |
| 6/9/03 | GHIJKL03 | 24.8 | 24.9 | YYY | | | | | | |
| 6/15/03 | GHIJKL03 | 24.8 | 24.6 | XXX | | | | | | |
| 6/17/03 | GHIJKL03 | 24.8 | 24.4 | XXX | | | | | | |
| 6/19/03 | GHIJKL03 | 24.8 | 24.8 | YYY | 24.8 | 25.5 | 24.0 | | 24.8 | |
| 7/1/03 | GHIJKL03 | 24.8 | 24.9 | YYY | 24.8 | 25.3 | 23.8 | | 24.8 | |
| 7/4/03 | GHIJKL03 | 24.8 | 24.6 | YYY | 24.8 | 25.3 | 23.8 | | 24.7 | |
| 7/8/03 | GHIJKL03 | 24.8 | 24.4 | XXX | 24.8 | 25.3 | 23.8 | | 24.6 | |
| 7/15/03 | GHIJKL03 | 24.8 | 24.2 | ZZZ | 24.8 | 25.3 | 23.8 | | 24.4 | |

TABLE 1-continued

| 7/21/03 | GHIJKL03 | 24.8 | 24.6 | ZZZ | 24.8 | 25.3 | 23.8 | 24.5 |
| 7/24/03 | GHIJKL03 | 24.8 | 24.8 | XXX | 24.8 | 25.3 | 23.8 | 24.6 |
| 8/1/03 | GHIJKL03 | 24.8 | 24.6 | ZZZ | 24.8 | 25.3 | 23.8 | 24.6 |
| 8/6/03 | GHIJKL03 | 24.8 | 25.1 | YYY | 24.8 | 25.3 | 23.8 | 24.8 |
| 8/12/03 | GHIJKL03 | 24.8 | 25.0 | XXX | 24.8 | 25.3 | 23.8 | 24.9 |
| 8/16/03 | GHIJKL03 | 24.8 | 25.1 | XXX | 24.8 | 25.3 | 23.8 | 25.0 |
| 8/19/03 | GHIJKL03 | 24.8 | 24.9 | XXX | 24.8 | 25.3 | 23.8 | 24.9 |
| 8/30/03 | GHIJKL03 | 24.8 | 24.9 | ZZZ | 24.8 | 25.3 | 23.8 | 24.9 |
| 9/5/03 | GHIJKL03 | 24.8 | 24.9 | YYY | 24.8 | 25.3 | 23.8 | 24.9 |
| 9/9/03 | GHIJKL03 | 24.8 | 25.0 | YYY | 24.8 | 25.3 | 23.8 | 24.9 |
| 9/15/03 | GHIJKL03 | 24.8 | 25.0 | XXX | 24.8 | 25.3 | 23.8 | 25.0 |
| 10/15/03 | GHIJKL03 | 24.8 | 24.9 | XXX | 24.8 | 25.3 | 23.8 | 24.9 |

7) >8 consecutive points on same side of mean line. Could signify change in quality.

Preferred Method for Data Analysis

While useful, the statistical techniques described herein above may be cumbersome, and produce too many flags. A preferred statistical method uses an EWMA (Exponential Weighted Moving Average) predictive algorithm to generate a prediction of a property value for some period in the future from the last data sample obtained. The forward prediction period can be selected to optimize business objectives. A period of 30 days will be assumed for the discussion herein below.

EWMA Algorithm Summary

Crude quality can be monitored using an autoregression based statistical model. Examples of autoregression models have been discussed by Koehler, Marks and O'Connell ("EWMA control chars for autoregressive process", Journal of the Operational Society, 52 (2001) 699-707) and by English, Lee and Martin ("Detecting changes in autoregressive processes with X-Bar and EWMA charts", IIE Transactions, 32 (2000), 1103-1113). For each crude grade that has sufficient crude monitoring data, the following statistical analysis is performed periodically. The period is optimized to meet business objectives.

1. The sample data set used for the statistics are samples taken in the last 12 months
2. A 30 day forward predicted EWMA (Exponential Weighted Moving Average) is calculated ($EWMA_{[30]}$), along with the RMSE (Root-Mean Square Error). The q parameter in the EWMA expression is optimized to provide the optimal forward prediction. Periods other than 30 days could be used.
3. Using the normal distribution probability function and the RMSE, the probability, TP, of a crude cargo falling within the $EWMA_{[30]} \pm R$ is calculated. Given the reproducibility of the property measurement, R, TP is considered to be the theoretical probability for a new Recommended Assay would have a property value equal to the $EWMA_{[30]}$ prediction.
3. Again, using the normal distribution probability function centered at $EWMA_{[30]}$, and with standard deviation RMSE, the probability, CP, of a crude cargo falling within the range from $PV_{RA}-R$ to $PV_{RA}+R$ around the current Recommended Assay property value, $PV_{RA}$ is calculated is calculated.
4. Using the t-distribution, $EWMA_{[30]}$, and RMSE, a $t_{test}$ value is calculated. Based on the $t_{test}$ value, a probability $p_{test}$ value is calculated.
5. Finally, using the normal distribution probability function centered at the $EWMA_{[30]}$, with standard deviation RMSE, Upper and Lower Control Limits (UCL and LCL) are calculated for a 1-α Confidence Interval. A 1-α probability of 90% may be used.
6. The $EWMA_{[30]}$, TP, CP, and $t_{test}$ value are the primary statistical parameters used to generate the flags/triggers, thresholds, and monitoring metrics to evaluate the current grade quality versus the Recommended Assay value. The flags/triggers developed from these primary statistics are:

$EWMA_{[30]}$ value falling outside the range form $PV_{RA}-R$ to $PV_{RA}+RA$ $p_{test}$ value falling below a critical $\alpha_{p\text{-}test}$ level. For an $\alpha_{p\text{-}test}$ value of 0.3, a $p_{test}$ value less than $\alpha_{p\text{-}test}$ would indicate a greater than 70% probability that a new Recommended Assay value would differ from the current Recommended assay value by a statistically significant amountA Recommended Assay, $PV_{RA}$, value falling outside the $EWMA_{[30]}$ Confidence Interval An increase in the ratio of TP to CP.

EWMA Statistics Calculations

The statistical calculations are performed in the following sequence.

Sample Set

Statistics are generated for each Grade, or each Grade/Loadport where there is a Loadport specific Recommended Assay, providing there is sufficient data. Data sufficiency is covered in a later section.

The sample data set used for the statistics are samples taken in the last 12 months, per the following sample preference:

1. All Loadport samples
2. If the data is primarily Discharge Port samples, then the discharge port data is used instead of Loadport data.
3. If neither 1. nor 2. provide sufficient data, then all samples are used.

Data Preparation

1. Prior to EWMA calculation, data may be screened for outliers using techniques described above.
2. Sort sample data in ascending date order. The earliest data point is index 0, the last point is index n. Each point has a date offset in days from the first point, e.g. if three samples had the dates Jan. 3, 2009, 01/04/09, and Jan. 10, 2009, the offsets would be 0, 1, and 7, respectively.
   Note: where multiple data points are reported on the same date, they are to be included as separate points with equal offsets
3. The number of total data points is saved as TotNumPoints=n+1

4. The index of the first data point with an offset greater than 29 is saved as Plus30StartIndex (m in equation subscripts). The number of data points with an offset greater than 29 is saved as NumPlus30Points. NumPlus30Points=n−Plus30StartIndex+1

Data Sufficiency

Statistics are not calculated if NumPlus30Points is less than 3.

EWMA$_{[30]}$ and RMSE

EWMA Calculation

EWMA$_{[30]}$ and RMSE are calculated through an optimization which seeks the EWMA weighting factor q that minimizes the RAISE. For a given value of q, EWMA$_i$ and EWMA$_{[30]}$ are calculated as EWMA$_0$=PV$_0$(PV$_i$=sample property value at data index i)

$$EWMA_1 = (1-q)*EWMA_0 + q*PV_1$$

...

$$EWMA_n = (1-q)*EWMA_{n-1} + q*PV_n$$

$$EWMA_{[30]} = EWMA_n$$

RMSE Calculation

RSME uses the minimum Resid$_q$ where q is the EWMA weighting factor, which can range from 0.0 to 1.0

Resid$_q$ is a sum squared residual calculated using the difference between the PV value of the subject data point (e.g. PV$_n$) and the EWMA of the match point which is the latest data point preceding the subject data point by more than 30 days. The subject data points are the data points with indexes from Plus30StartIndex (or m) to n.

$$Resid_q = (PV_m - EWMA_{i(m)})^2 + (PV_{m+1} - EWMA_{i(m+1)})^2 + \ldots + (PV_n - EWMA_{i(n)})^2$$

where i(m), i(m+1), . . . , i(n) denote the index of the match point associated with the target point.

Resid$_q$ is calculated for values of q between 0 and 1, and the value q$_{min}$ which produces the minimum value of Resid$_q$ is selected. This minimum Resid$_q$ is designated Resid$_{min}$. RMSE is the Root Mean Square Error, or the variance associated with the measurement reproducibility (R/2.77), whichever is greater.

$$RMSE = \max\left(\sqrt{\frac{Resid_{min}}{NumPlus\,30\,Points}}, \frac{R}{2.77}\right)$$

t-Test (pValue) Calculation

A t$_{test}$ value is calculated based on the difference between the forward predicted EWMA value, and the property value for the Recommended Assay, PV$_{RA}$ $$t_{test} = \frac{|EWMA_{[30]} - PV_{RA}|}{RMSE\sqrt{\frac{1+100\,q}{200-100\,q}}}$$

A probabilty p$_{test}$ value is calculated based on a t-distribution with NumPlus30Points degrees of freedom.

$$p_{test} = 2\left(1 - \int_{-\infty}^{t_{test}} f(t)\,dt\right)$$

$$\text{where } f(t) = \frac{\Gamma\left(\frac{v+1}{2}\right)}{\sqrt{v\pi}\,\Gamma\left(\frac{v}{2}\right)}\left(1 + \frac{t^2}{v}\right)^{-\left(\frac{v+1}{2}\right)}$$

is the t-distribution and v is NumPlus30Points degrees of freedom. p$_{test}$ test represents the probability that, given RMSE, q and NumPlus30Points, a new Recommended Assay PV value would differ from the Recommended Assay property value, PV$_{RA}$ by less than |EWMA$_{[30]}$−PV$_{RA}$|, and is a measure of the statistical significance of the EWMA$_{[30]}$ estimate.

Theoretical and Current Recommended Assay Sample Probability

A TP (theoretical) and CP (current) Recommended Assay sample probability are calculated as:

$$TP = \int_{EWMA_{[30]}-R}^{EWMA_{[30]}+R} \varphi(x, \mu, \sigma)\,dx \text{ and}$$

$$CP = \int_{PV_{RA}-R}^{PV_{RA}+R} \varphi(x, \mu, \sigma)\,dx$$

where φ(x, μ, σ) is the normal (Gaussian) distribution $$\varphi(x, \mu, \sigma) = \frac{1}{\sigma\sqrt{2\pi}}e^{-(x-\mu)^2/2\sigma^2}$$

with mean μ=EWMA$_{[30]}$ and standard deviation σ=RMSE. TP represents the probability, given RAISE and the property measurement method reproducibility, R, that the property value, PV, will be within the range from EWMA$_{[30]}$−R to EWMA$_{[30]}$+R. CP represents the probability, given EWMA$_{[30]}$, RMSE and R, that the crude property value will be within the range from PV$_{RA}$−R to PV$_{RA}$+R.

Figures 5A, 5B:
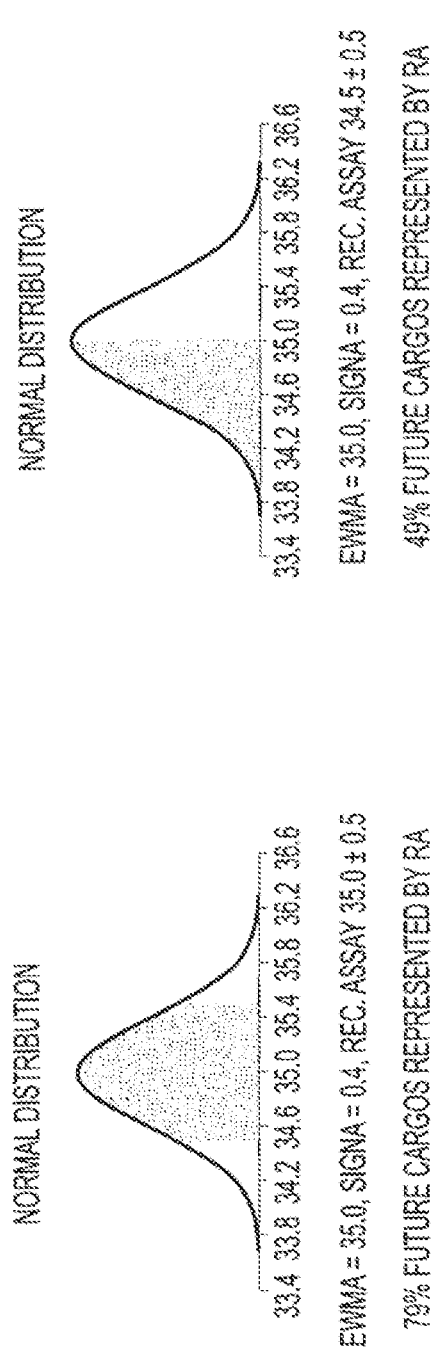
FIGS. 5a and 5b show a statistical analysis of the Recommended Assay.

The use of TP for deciding whether to update a Recommended Assay is illustrated in the following example. The process described above is applied to API Gravity for a crude oil. R for API Gravity is 0.5. If the Recommended Assay had an API Gravity of 35, if an EWMA$_{[30]}$ value of 35 and an RMSE value of 0.4 are determined, then the Recommended Assay is expected to be representative of 79% of future cargoes (FIG. 5a). If however, the Recommended Assay value was 34.5, then the same EWMA$_{[30]}$ and RMSE values would indicate that the Recommended Assay was only expected to be representative of 49% of future cargoes. Updating the Recommended Assay could improve coverage by 30%.

Upper/Lower 90% Confidence Interval Control Limits

Confidence Interval Control Limits are calculate as:

UCL=EWMA$_{[30]}$+RSME*t(1−a,NumPlus30Points)

LCL=EWMA$_{[30]}$−RSME*t(1−a,NumPlus30Points)

Where, t(1−α, v) is the t-distribution value for cumulative probability of 1−α, and degrees of freedom v. An α value of 0.1 can be used.

Example $EWMA_{[30]}$ statistical calculations are shown in Table 2. Data shown are API value for a crude from a single load port over a one year period. A q value of 0.03 is shown to minimize $Resid_q$ Automatic User Notification of Significant Quality Changes Significant quality deviation are recorded identifying the crude oil grade, quality, and date of detection. In accordance with the presently disclosed subject matter, the computer system performs the above described comparisons and applies the above described statistical techniques (e.g., the EWMA method). If a significant deviation is detected, the computer may generate a notification for the appropriate users such that they are notified to evaluate each of the identified quality deviations. Depending upon the quality deviation, the individual charged with reviewing this data would take appropriate action to ensure the situation is appropriately addressed. The appropriate action may be implemented by either the user or automatically by the controller in the computer system.

Possible actions can include:

Changing the Recommended Assay because a change in crude oil quality has been detected Obtain additional data to ensure that identified quality changes are sustained Ignoring the deviation if it is determined to be a temporary change in crude oil quality Apply Gate Value Differential Between Global Standard Assay and Current Assay Based on Quality Changes Gate Values are estimates of crude value made based on crude quality information. Refinery Gate Value is defined as:

$$GateValue = \sum_{products} ProductYield * ProductPrices \pm ProductQualityAdjustments$$

Gate value is typically calculated using generalized (vector) refinery models based on estimates of crude quality. Gate Values are widely used within the petroleum industry, and software/models for calculating gate values are commercially available (see for instance Argus Netback Model at www.argusmediagroup.com).

TABLE 2

Example of EWMA Statistical Calculations

| Tot Num Points | Num Plus 30 Points | q | | | | | | |
|---|---|---|---|---|---|---|---|---|
| | | 0.02 | Resid-q 3.41984 | 0.03 | Resid-q 3.41742 | 0.04 | Resid-q 3.42172 | |
| 62 | 55 | | | | | | | |
| | 56 | | | | | | | |

| Index | Highest Index Preceding Current Date by >=30 days | Q | EWMA | EWMA (i(m)) | Diff Squared | EWMA | EWMA (i(m)) | Diff Squared | EWMA | EWMA (i(m)) | Diff Squared |
|---|---|---|---|---|---|---|---|---|---|---|---|
| 0 | | | 27.60 | | | 27.60 | | | 27.60 | | |
| 1 | | | 27.60 | | | 27.60 | | | 27.60 | | |
| 2 | | | 27.60 | | | 27.60 | | | 27.60 | | |
| 3 | | | 27.60 | | | 27.61 | | | 27.61 | | |
| 4 | | | 27.60 | | | 27.61 | | | 27.61 | | |
| 5 | | | 27.61 | | | 27.61 | | | 27.61 | | |
| 6 | | | 27.61 | | | 27.61 | | | 27.61 | | |
| 7 | 8 | Plus30 Start Index | 27.61 | 27.60 | 0.01 | 27.61 | 27.60 | 0.01 | 27.62 | 27.60 | 0.01 |
| 8 | 8 | | 27.61 | 27.60 | 0.01 | 27.62 | 27.60 | 0.01 | 27.62 | 27.60 | 0.01 |
| 9 | 39 | | 27.61 | 27.61 | 0.01 | 27.62 | 27.61 | 0.01 | 27.62 | 27.62 | 0.01 |
| 10 | 39 | | 27.61 | 27.61 | 0.01 | 27.62 | 27.61 | 0.01 | 27.63 | 27.62 | 0.01 |
| 11 | 39 | | 27.62 | 27.61 | 0.04 | 27.63 | 27.61 | 0.03 | 27.63 | 27.62 | 0.03 |
| 12 | 39 | | 27.62 | 27.61 | 0.04 | 27.63 | 27.61 | 0.03 | 27.64 | 27.62 | 0.03 |
| 13 | 80 | | 27.62 | 27.61 | 0.01 | 27.63 | 27.62 | 0.01 | 27.64 | 27.62 | 0.02 |
| 14 | 80 | | 27.62 | 27.61 | 0.01 | 27.62 | 27.62 | 0.01 | 27.63 | 27.62 | 0.02 |
| 15 | 80 | | 27.63 | 27.61 | 0.22 | 27.64 | 27.62 | 0.21 | 27.65 | 27.62 | 0.21 |
| 16 | 80 | | 27.64 | 27.61 | 0.26 | 27.65 | 27.62 | 0.25 | 27.67 | 27.62 | 0.25 |
| 17 | 80 | | 27.63 | 27.61 | 0.01 | 27.65 | 27.62 | 0.01 | 27.66 | 27.62 | 0.02 |
| 18 | 104 | | 27.63 | 27.62 | 0.00 | 27.65 | 27.63 | 0.00 | 27.66 | 27.64 | 0.00 |
| 19 | 104 | | 27.63 | 27.62 | 0.01 | 27.65 | 27.63 | 0.00 | 27.66 | 27.64 | 0.00 |
| 20 | 120 | | 27.63 | 27.63 | 0.00 | 27.65 | 27.65 | 0.00 | 27.66 | 27.66 | 0.00 |
| 21 | 120 | | 27.63 | 27.63 | 0.00 | 27.65 | 27.65 | 0.00 | 27.65 | 27.66 | 0.00 |
| 22 | 138 | | 27.63 | 27.63 | 0.05 | 27.64 | 27.65 | 0.06 | 27.64 | 27.66 | 0.07 |
| 23 | 143 | | 27.63 | 27.63 | 0.00 | 27.64 | 27.65 | 0.00 | 27.64 | 27.66 | 0.00 |
| 24 | 143 | | 27.63 | 27.63 | 0.02 | 27.63 | 27.65 | 0.02 | 27.64 | 27.66 | 0.03 |
| 25 | 143 | | 27.62 | 27.63 | 0.05 | 27.63 | 27.65 | 0.06 | 27.63 | 27.66 | 0.07 |
| 26 | 143 | | 27.62 | 27.63 | 0.05 | 27.62 | 27.65 | 0.06 | 27.62 | 27.66 | 0.07 |
| 27 | 143 | | 27.63 | 27.63 | 0.39 | 27.64 | 27.65 | 0.37 | 27.64 | 27.66 | .036 |
| 28 | 166 | | 27.63 | 27.63 | 0.00 | 27.64 | 27.65 | 0.00 | 27.65 | 27.66 | 0.00 |
| 29 | 166 | | 27.63 | 27.63 | 0.00 | 27.64 | 27.65 | 0.00 | 27.65 | 27.66 | 0.00 |
| 30 | 173 | | 27.64 | 27.63 | 0.32 | 27.66 | 27.64 | 0.30 | 27.67 | 27.64 | 0.30 |
| 31 | 173 | | 27.64 | 27.63 | 0.02 | 27.65 | 27.64 | 0.02 | 27.66 | 27.64 | 0.02 |
| 32 | 178 | | 27.64 | 27.63 | 0.05 | 27.65 | 27.64 | 0.06 | 27.65 | 27.64 | 0.06 |

TABLE 2-continued

Example of EWMA Statistical Calculations

| 33 | 187 | 27.65 | 27.63 | 0.25 | 27.66 | 27.64 | 0.24 | 27.67 | 27.64 | 0.24 |
|---|---|---|---|---|---|---|---|---|---|---|
| 34 | 187 | 27.64 | 27.63 | 0.02 | 27.66 | 27.64 | 0.02 | 27.67 | 27.64 | 0.02 |
| 35 | 187 | 27.64 | 27.63 | 0.02 | 27.65 | 27.64 | 0.02 | 27.66 | 27.64 | 0.02 |
| 36 | 210 | 27.64 | 27.64 | 0.00 | 27.65 | 27.65 | 0.00 | 27.66 | 27.65 | 0.00 |
| 37 | 210 | 27.64 | 27.64 | 0.00 | 27.65 | 27.65 | 0.00 | 27.66 | 27.65 | 0.00 |
| 38 | 210 | 27.63 | 27.64 | 0.19 | 27.64 | 27.65 | 0.20 | 27.64 | 27.65 | 0.21 |
| 39 | 210 | 27.62 | 27.64 | 0.11 | 27.63 | 27.65 | 0.12 | 27.63 | 27.65 | 0.12 |
| 40 | 222 | 27.63 | 27.64 | 0.00 | 27.63 | 27.66 | 0.00 | 27.63 | 27.67 | 0.00 |
| 41 | 222 | 27.63 | 27.64 | 0.09 | 27.64 | 27.66 | 0.09 | 27.64 | 27.67 | 0.08 |
| 42 | 222 | 27.63 | 27.64 | 0.02 | 27.63 | 27.66 | 0.02 | 27.63 | 27.67 | 0.03 |
| 43 | 246 | 27.63 | 27.64 | 0.00 | 27.63 | 27.65 | 0.00 | 27.63 | 27.66 | 0.00 |
| 44 | 246 | 27.63 | 27.64 | 0.00 | 27.63 | 27.65 | 0.00 | 27.63 | 27.66 | 0.00 |
| 45 | 250 | 27.63 | 27.62 | 0.00 | 27.63 | 27.63 | 0.00 | 27.63 | 27.63 | 0.00 |
| 46 | 250 | 27.63 | 27.62 | 0.11 | 27.64 | 27.63 | 0.10 | 27.64 | 27.63 | 0.10 |
| 47 | 250 | 27.64 | 27.62 | 0.01 | 27.64 | 27.63 | 0.01 | 27.65 | 27.63 | 0.01 |
| 48 | 256 | 27.63 | 27.63 | 0.00 | 27.64 | 27.63 | 0.00 | 27.64 | 27.63 | 0.00 |
| 49 | 262 | 27.63 | 27.63 | 0.02 | 27.64 | 27.64 | 0.02 | 27.64 | 27.64 | 0.02 |
| 50 | 271 | 27.63 | 27.63 | 0.02 | 27.63 | 27.63 | 0.02 | 27.63 | 27.63 | 0.02 |
| 51 | 285 | 27.64 | 27.63 | 0.29 | 27.65 | 27.64 | 0.28 | 27.65 | 27.64 | 0.28 |
| 52 | 286 | 27.63 | 27.64 | 0.11 | 27.64 | 27.64 | 0.12 | 27.64 | 27.65 | 0.12 |
| 53 | 286 | 27.63 | 27.64 | 0.11 | 27.63 | 27.64 | 0.12 | 27.63 | 27.65 | 0.12 |
| 54 | 291 | 27.63 | 27.63 | 0.04 | 27.63 | 27.64 | 0.04 | 27.63 | 27.64 | 0.03 |
| 55 | 291 | 27.63 | 27.63 | 0.02 | 27.63 | 27.64 | 0.02 | 27.63 | 27.64 | 0.02 |
| 56 | 302 | 27.63 | 27.63 | 0.02 | 27.63 | 27.63 | 0.02 | 27.62 | 27.63 | 0.02 |
| 57 | 302 | 27.63 | 27.63 | 0.07 | 27.63 | 27.63 | 0.07 | 27.63 | 27.63 | 0.07 |
| 58 | 319 | 27.64 | 27.63 | 0.27 | 27.65 | 27.64 | 0.26 | 27.66 | 27.64 | 0.26 |
| 59 | 324 | 27.64 | 27.63 | 0.02 | 27.65 | 27.63 | 0.02 | 27.65 | 27.63 | 0.02 |
| 60 | 330 | 27.64 | 27.63 | 0.02 | 27.64 | 27.63 | 0.02 | 27.64 | 27.63 | 0.02 |
| 61 | 334 | 27.64 | 27.63 | 0.01 | 27.64 | 27.63 | 0.01 | 27.65 | 27.62 | 0.01 |

Figure 7:
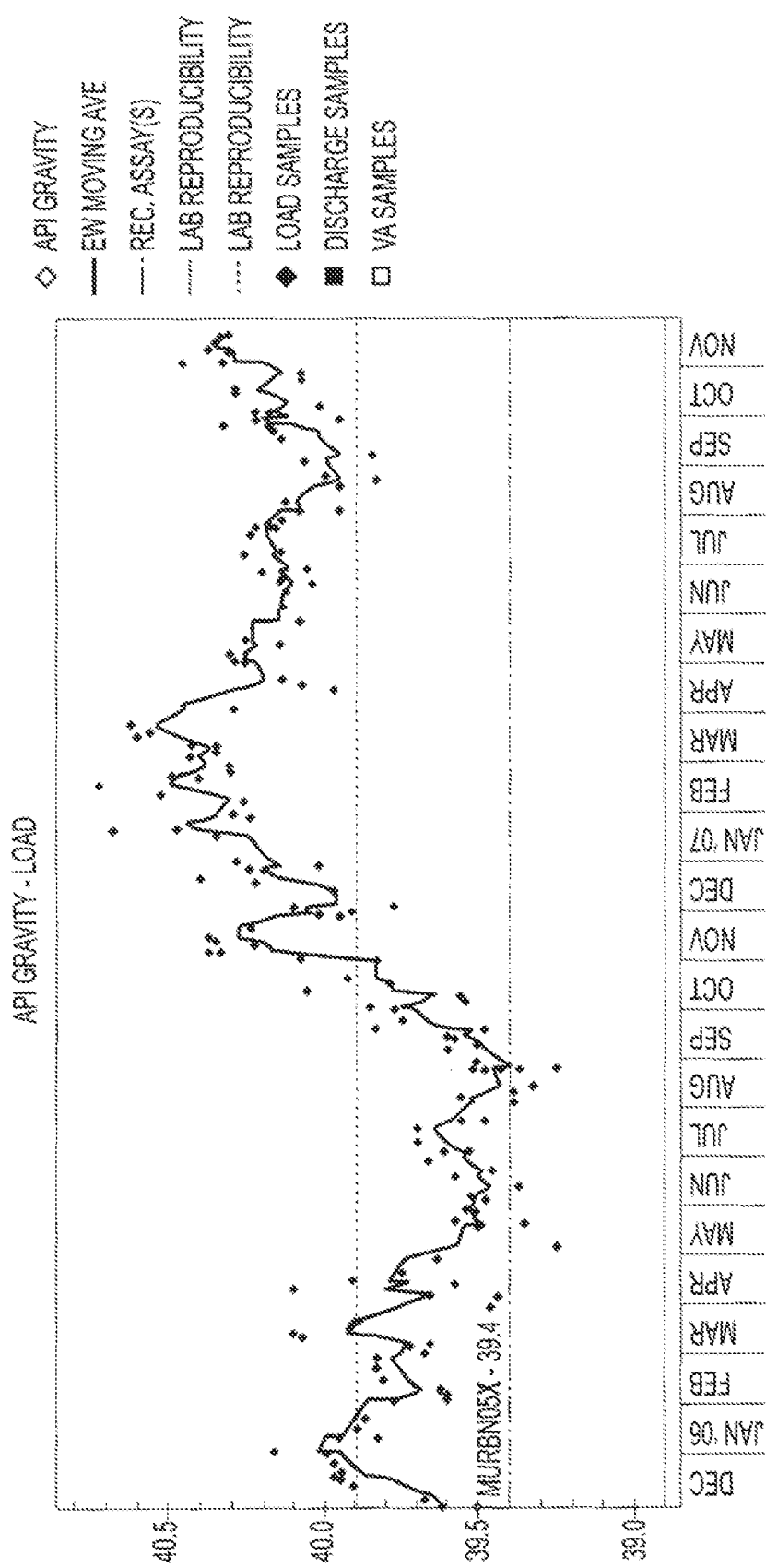
FIG. 7 shows a time series of crude oil monitoring data for API gravity of Murban crude oil.
Figure 8:
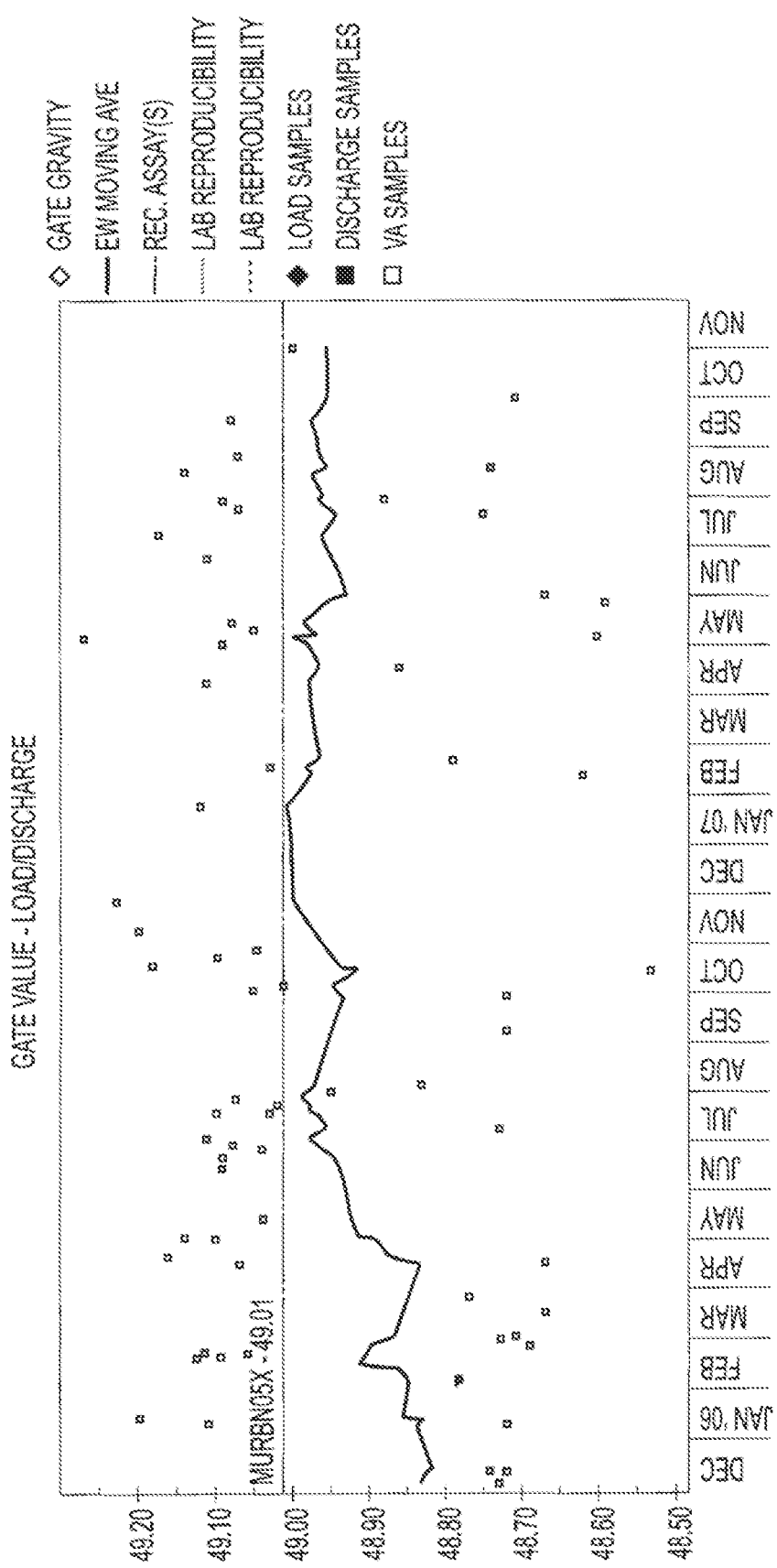
FIG. 8 shows a time series of crude oil monitoring data for gate value of Murban crude oil.

Some significant quality changes do not have material impact on crude oil values. FIG. 7 shows the time series API gravity data for Murban crude oil from December 2005, through November 2007. The API gravity demonstrated a significant change from the Recommended Assay value of 39.4 API gravity during 3Q06 to an average value of approximately 40.3 API gravity during the second half of 2007. The gate value differential during this time, shown in FIG. 8, was less than 0.10 $/B absolute. The change was due to small shifts in the yield structure of the crude which affected the API Gravity, but had a negligible economic impact.

Conversely, crude oil gate value may change significantly while typical crude quality indicators such as API gravity show little variation. Therefore, Virtual Assay or alternative techniques can be utilized to determine the crude oil value compared to the Recommended Assay and trending this over time will provide additional information that can be used to identify and prioritize potential assay updates.

Figure 9:
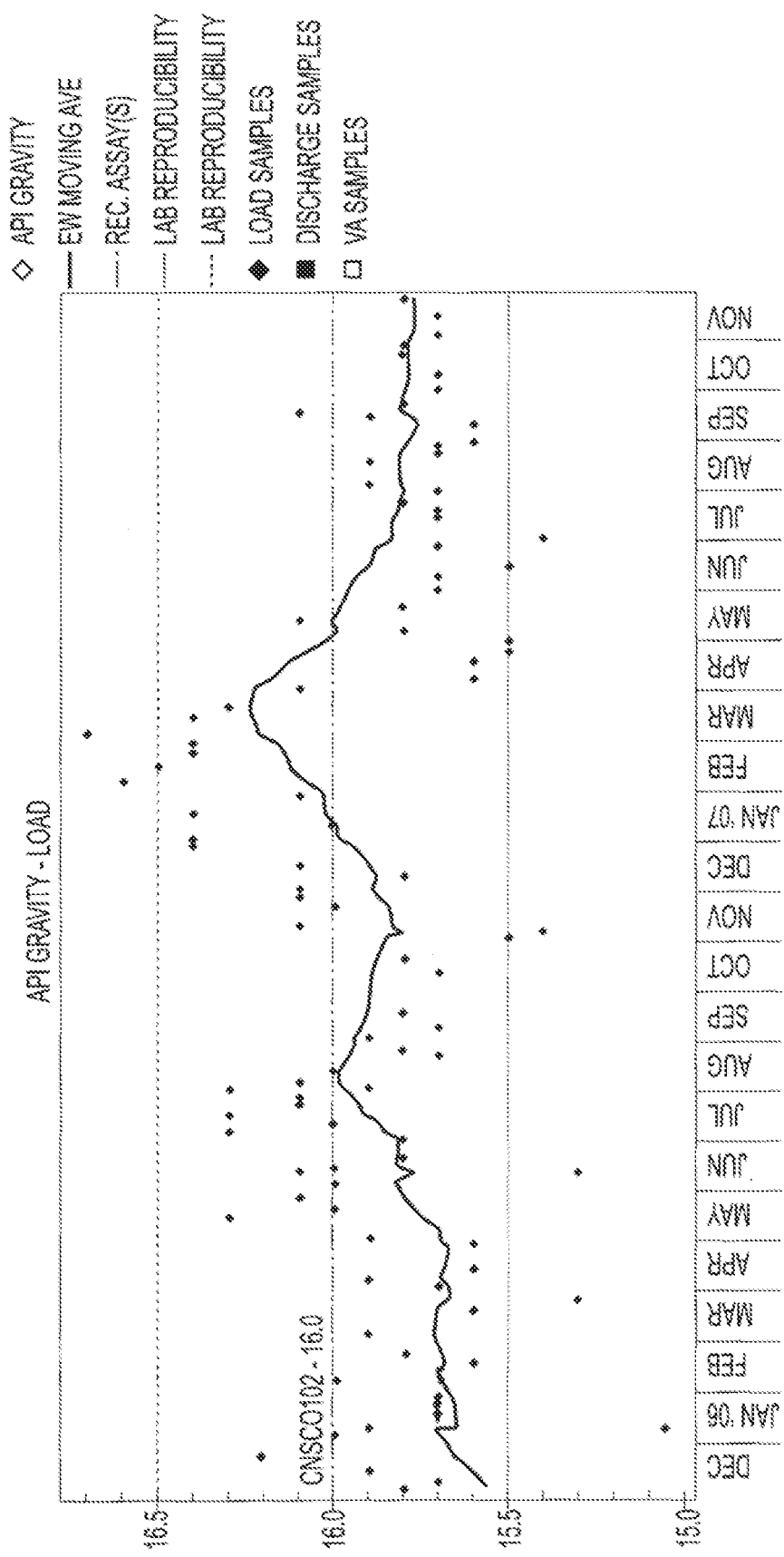
FIG. 9 shows a time series of crude oil monitoring data for API gravity of Cerro Negro SCO.
Figure 10:
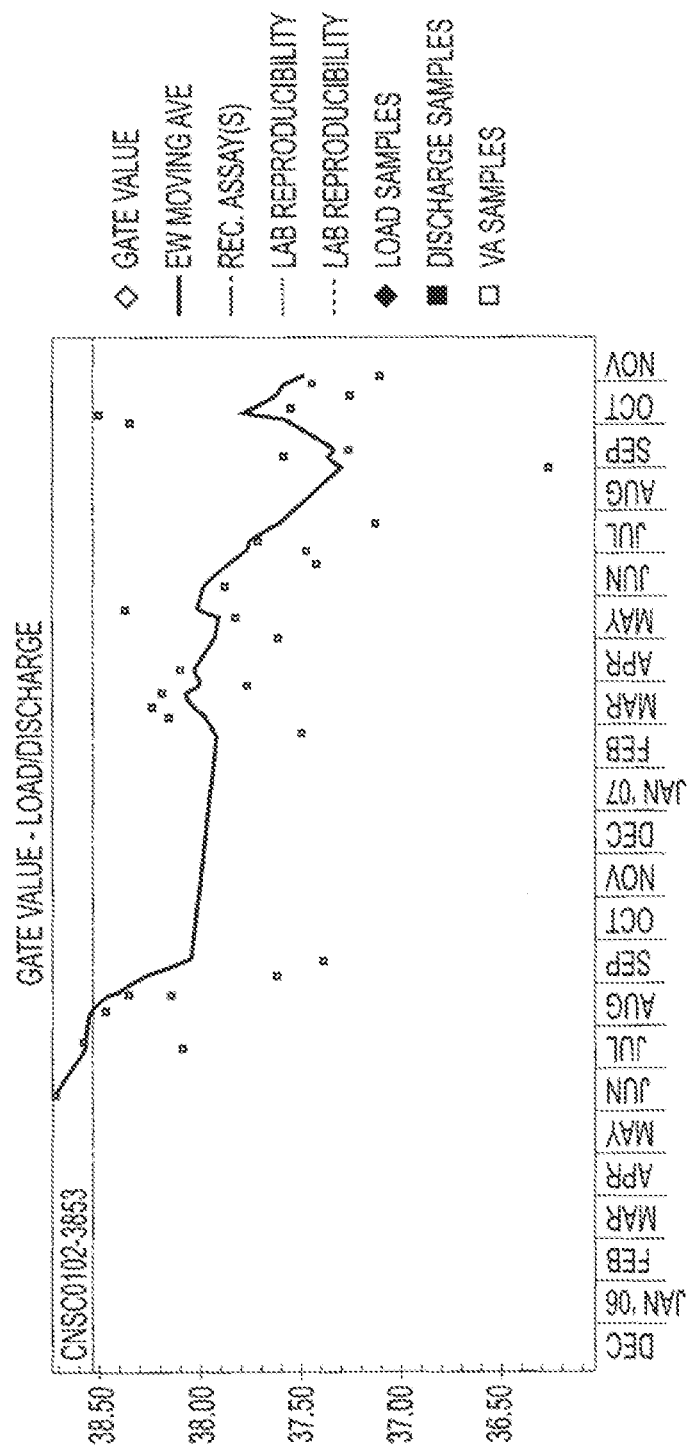
FIG. 10 shows a time series of crude oil monitoring data for value differential of Cerro Negro SCO.
Figure 11:
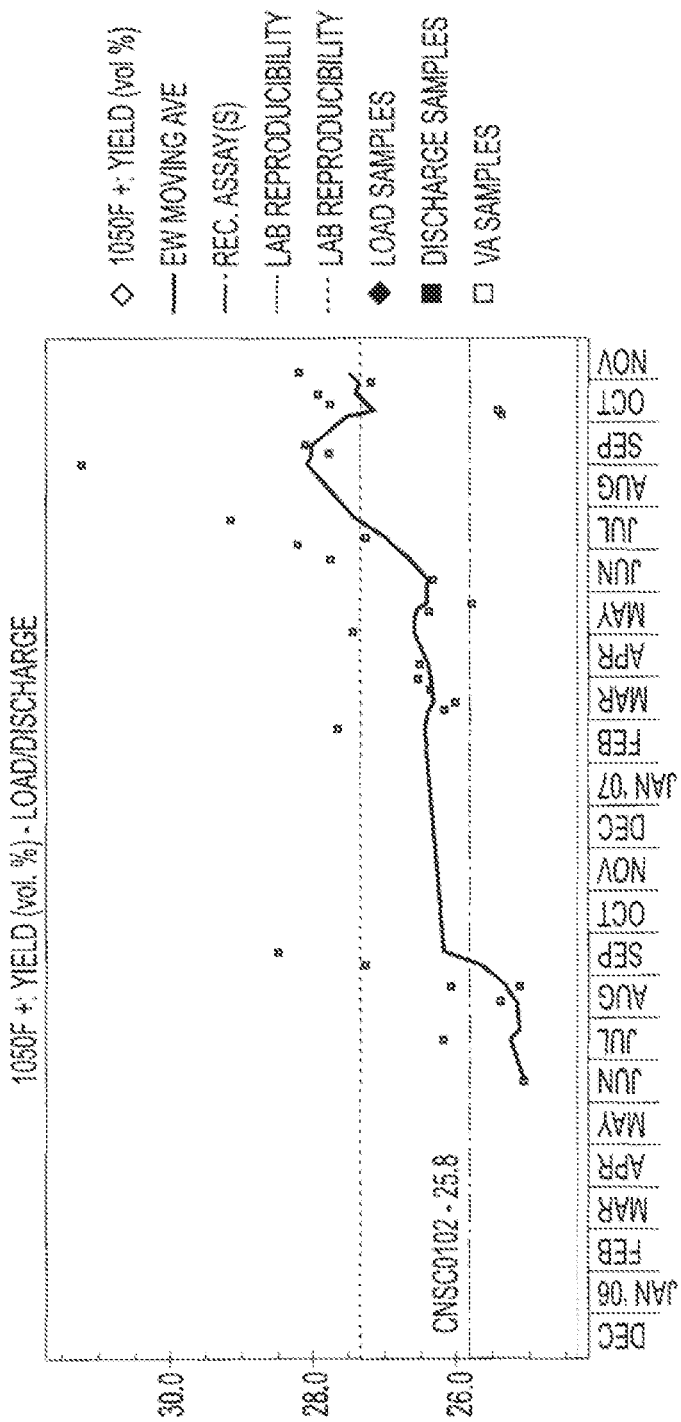
FIG. 11 shows a time series of crude oil monitoring data for 1050+F resid yield of Cerro Negro SCO.
Figure 12:
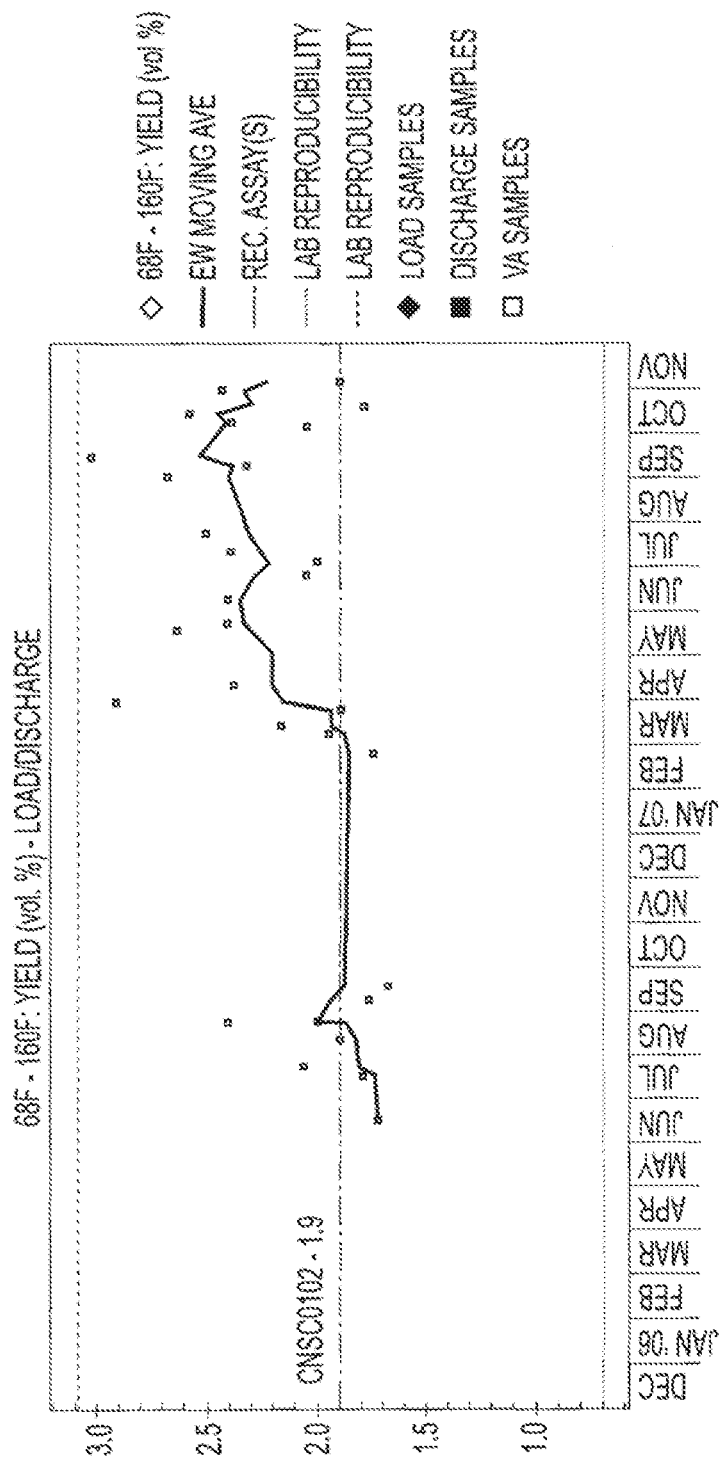
FIG. 12 shows a time series of crude oil monitoring data for API gravity at a later time of Cerro Negro SCO.

FIG. 9 provides an example that API gravity of Cerro Negro SCO over time has not demonstrated a significant change. However, as shown in FIG. 10, the delta value between current crude oil quality versus the Recommended Assay demonstrates a crude oil value decrease of approximately 1.00 $/B. This change was due to an increase in 1050+F resid yield of approximately 2% absolute as indicated in FIG. 11. The API gravity did not experience a significant increase since the resid yield was balanced by a increase in naphtha (68 F-160 F) yield as shown in FIG. 12.

Update Recommended Assay as Warranted

A primary objective of a crude oil monitoring program is to identify grades which require a Recommended Assay update. Once a determination has been made that an assay update is required, the monitoring information may be used to:

Implement the Virtual Assay information as the new Recommended Assay

Signal the need to obtain a crude oil sample for a new wet assay to develop the new Recommended Assay Define the acceptable range of the crude oil sample to be used for the new wet assay Employ Laboratory Checks to Ensure Consistency of Results A procedure to ensure consistency of the spectroscopic, physical property, and inspection tests results is required since numerous laboratories will be involved in the data generation. Consistency of spectroscopic data is ensured by application of methods such as those described in ASTM E1866. Consistency of physical property and inspection tests are ensured by application of quality assurance procedures such as those described in ASTM D6299.

A laboratory cross check program such as those implemented by ASTM designed to detect deviations beyond normal variations is implemented. If laboratory results are outside expected tolerances, then appropriate corrective action is required.

The presently disclosed subject matter is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method for monitoring global crude oil quality comprising:

obtaining at least one sample of a crude oil representative of the current quality of the crude oil;

analyzing the at least one sample of the crude oil and generating characterization data based upon the analyzing of the at least one sample by laboratory distillation, spectroscopic techniques, or a combination of spectroscopic techniques and physical inspections;

estimating values of properties of an assay of the crude oil by analyzing the generated characterization data from the at least one sample to form an estimated assay;

storing the estimated values of the properties of the estimated assay in a database;

determining deviations of the values of the properties of the estimated assay for the crude oil from the values of the properties of a known recommended assay for crude oil having a known quality, wherein the values of the properties of the known recommended assay are stored in the database wherein the known recommended assay is a single representation of yields and qualities used to characterize current crude oil quality;

determining a statistical significance of the deviations of the values of the properties of the estimated assay from the values of the properties of the recommended assay to determine if the crude oil quality of the at least one sample is different from the quality of the recommended assay;

generating a new recommended assay for the crude oil if the deviations of the values of the properties of the estimated assay from the values of the properties of the recommended assay are significant; and storing new recommended assay in the database.

2. The method of claim 1, wherein determining the statistical significance of the deviations of the values of the properties of the estimated assay from the values of the properties of the recommended assay includes determining if the statistical significance indicates a change in the economic valuation of the crude oil between the estimated assay and the recommended assay.

3. The method of claim 2 further comprising generating a notification if the economic difference is statistically significant.

4. The method of claim 2, wherein determining the statistical significance of the deviations of the values of the properties of the estimated assay from the values of the properties of the recommended assay includes detecting and removing values which may be outliers that may distort the statistical significance of the economic difference.

5. The method of claim 1, wherein determining deviations of the values of the properties of the estimated assay for the crude oil from the values of the properties of a known recommended assay for crude oil includes determining time series values for the properties of the estimated assay over a period of time.

6. The method of claim 5 further comprising comparing the properties of the time series values to values of the properties for the recommended assay.

7. The method of claim 1 wherein determining the statistical significance is carried out by an exponential weighted moving average predictive algorithm.

8. The method of claim 1, wherein storing the new recommended assay in the database includes replacing the known recommended assay with the new recommended assay.

9. The method of claim 1, wherein the estimated assay is one of a virtual assay and a modified virtual assay.

10. The method of claim 1, wherein generating the new recommended assay is generated from a wet crude oil assay.

11. The method of claim 1, wherein generating the new recommended assay is generated from a modified virtual assay.

* * * * *